United States Patent
Dilmanian et al.

[11] Patent Number: 5,818,050
[45] Date of Patent: Oct. 6, 1998

[54] COLLIMATOR-FREE PHOTON TOMOGRAPHY

[75] Inventors: F. Avraham Dilmanian, Yaphank; Randall L. Barbour, Westbury, both of N.Y.

[73] Assignee: Brookhaven Science Associates LLC, Upton, N.Y.

[21] Appl. No.: 838,493

[22] Filed: Apr. 7, 1997

[51] Int. Cl.$^6$ .................................................. G01T 1/166
[52] U.S. Cl. ................................ 250/363.09; 250/363.04
[58] Field of Search ...................... 250/363.09, 363.01, 250/363.02, 363.03, 363.04, 252.1 R

[56] References Cited

U.S. PATENT DOCUMENTS

| | | |
|---|---|---|
| 5,103,098 | 4/1992 | Fenimes . |
| 5,289,008 | 2/1994 | Jaszczak et al. ...................... 250/363 |
| 5,311,427 | 5/1994 | Ichihara ............................. 250/363.04 |
| 5,373,443 | 12/1994 | Lee et al. ................................ 364/420 |

OTHER PUBLICATIONS

Klibanov et al, "Newton–Kantorovich Method for Three–Dimensional Potential Inverse Scattering Problem and Stability of the Hyperbolic Cauchy Problem with Time–Dependent Data," *Inverse Problems*, vol. 7, pp. 577–596, 1991.

Chew et al, "Reconstruction of Two–Dimensional Permittivity Distribution Using the Distorted Born Iterative Method," *IEEE Transactions on Medical Imaging*, vol. 9, No. 2, pp. 218–225, 1990.

Yao et al, "Simultaneous Reconstruction of Absorption and Scattering Distributions in Turbid Media Using a Born Iterative Method," SPIE vol. 2570, Jul. 1995, pp. 96–107.

O'Leary et al, "Simultaneous Scattering and Absorption Images of Heterogeneous Media Using Diffusive Waves within the Rytov Approximation," SPIE vol. 2389, Feb. 1995, pp. 320–327.

*Primary Examiner*—Edward P. Westin
*Assistant Examiner*—Richard Hanig
*Attorney, Agent, or Firm*—Margaret C. Bogosian

[57] ABSTRACT

A method of uncollimated single photon emission computed tomography includes administering a radioisotope to a patient for producing gamma ray photons from a source inside the patient. Emissivity of the photons is measured externally of the patient with an uncollimated gamma camera at a plurality of measurement positions surrounding the patient for obtaining corresponding energy spectrums thereat. Photon emissivity at the plurality of measurement positions is predicted using an initial prediction of an image of the source. The predicted and measured photon emissivities are compared to obtain differences therebetween. Prediction and comparison is iterated by updating the image prediction until the differences are below a threshold for obtaining a final prediction of the source image.

19 Claims, 4 Drawing Sheets

COLLIMATOR-FREE PHOTON TOMOGRAPHY

This invention was made with Government support under contract number DE-AC02-76CH00016, awarded by the U.S. Department of Energy. The Government has certain rights in the invention.

The present invention relates generally to emission tomography in nuclear medicine, and, more specifically, to single photon emission computed tomography (SPECT) for imaging patients.

One type of emission tomographic system used in diagnostic nuclear medicine is the single photon emission computed tomography (SPECT) system in which a low activity gamma ray emitter is administered into the body of a patient by injection or inhalation. The gamma ray emitter may be any of the isotopes currently used in SPECT, including for example $^{99m}$Tc, in any conventional form. The radioisotope is selected for preferentially targeting a specific organ in the patient's body whose image is to be produced.

A suitable gamma ray camera or detector may detect only gamma rays emitted from the body normal to its face plane. The intensity of the detected gamma rays is digitally stored as a two dimensional image formed of discrete picture elements or pixels.

The gamma camera may take any conventional form, such as one or more flat plate cameras, or arcuate or completely annular cameras if desired, such as one or more Anger-type cameras rotating on a gantry. The camera typically includes a collimator which is typically a lead plate with a grid of narrow channels which define very narrow incidence angles for receiving gamma ray photons substantially perpendicularly or normal to the camera. A suitable scintillator, such as sodium iodide or bismuth germinate, is placed beneath the collimator for receiving the photons which produce light in the scintillator. Adjoining the scintillator are a plurality of light detectors, such as photomultipliers, photodiodes, or avalanche photodiodes which detect the intensity of the scintillation light produced by the gamma photons.

The gamma ray photons emitted from the source organ in the patient travel outside to the camera. In their travel out, they may or may not interact with the body tissue. The interaction can be one or multiple scattering, or a photoelectric interaction. The energy of the photons is maximum, or full energy, for the unscattered travel, and decreases in each scattering. In conventional SPECT systems, a data acquisition system or electronics typically evaluates the energy of the individual gamma photon events detected in the camera, and accepts only those events inside a specific energy window centered around the full energy of the particular radioisotope's energy line to identify unscattered photons. Therefore, only unscattered photon events are counted over a specified sample time for providing an indication of the intensity of the detected photons which corresponds with the cumulative count thereof.

The gamma camera detects photons in a two dimensional plane. In Anger-type cameras, the scintillation light from the NaI(TI) plate is detected by many of the individual detectors for simultaneously detecting an individual photon event. The data acquisition system then accurately determines the spatial location of the incident photon by determining a center of gravity-type position within the two dimensional array of photodetectors. In this way, a projection image of the radiating organ source may be obtained by the camera at a specific measurement position thereof.

The gamma camera is typically indexed or rotated about the patient for obtaining corresponding projection views or images completely around the patient in 360°. The several images detected by the camera are then computer processed to reconstruct tomographic images or pictures of the source organ in many transaxial slices of the body within a finite height of the body corresponding with the height of the gamma camera.

In order to avoid adverse effects of radiation due to the radioisotope, the radiation dosage thereof is minimized as much as possible. The lower the radiation dosage, the more time it takes to collect a suitable number of photon events at each angular measurement of the camera for a desired statistical significance of the results. For example, collecting one hundred and twenty-eight views spaced apart at 2.8°, with a sample time of about 20 seconds per view requires about forty minutes to complete the full scan. Since a typical image pixel in the gamma camera is about a 2 mm square, movement of the patient of this magnitude will distort or blur the detected image since it is difficult to remain still for the entire sample time, let alone the entire scan time.

Accordingly, it is desirable to improve photon computer tomography by reducing either the data acquisition time, or reducing radioisotope dosage, or both, while still maintaining effective contrast and spatial resolution of the scanned image.

SUMMARY OF THE INVENTION

A method of uncollimated single photon emission computed tomography includes administering a radioisotope to a patient for producing gamma ray photons from a source inside the patient. Emissivity of the photons is measured externally of the patient with an uncollimated gamma camera at a plurality of measurement positions surrounding the patient for obtaining corresponding energy spectrums thereat. Photon emissivity at the plurality of measurement positions is predicted using an initial prediction of an image of the source. The predicted and measured photon emissivities are compared to obtain differences therebetween. Prediction and comparison is iterated by updating the image prediction until the differences are below a threshold for obtaining a final prediction of the source image.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DESCRIPTION OF THE PREFERRED EMBODIMENT(S)

Figure 1:
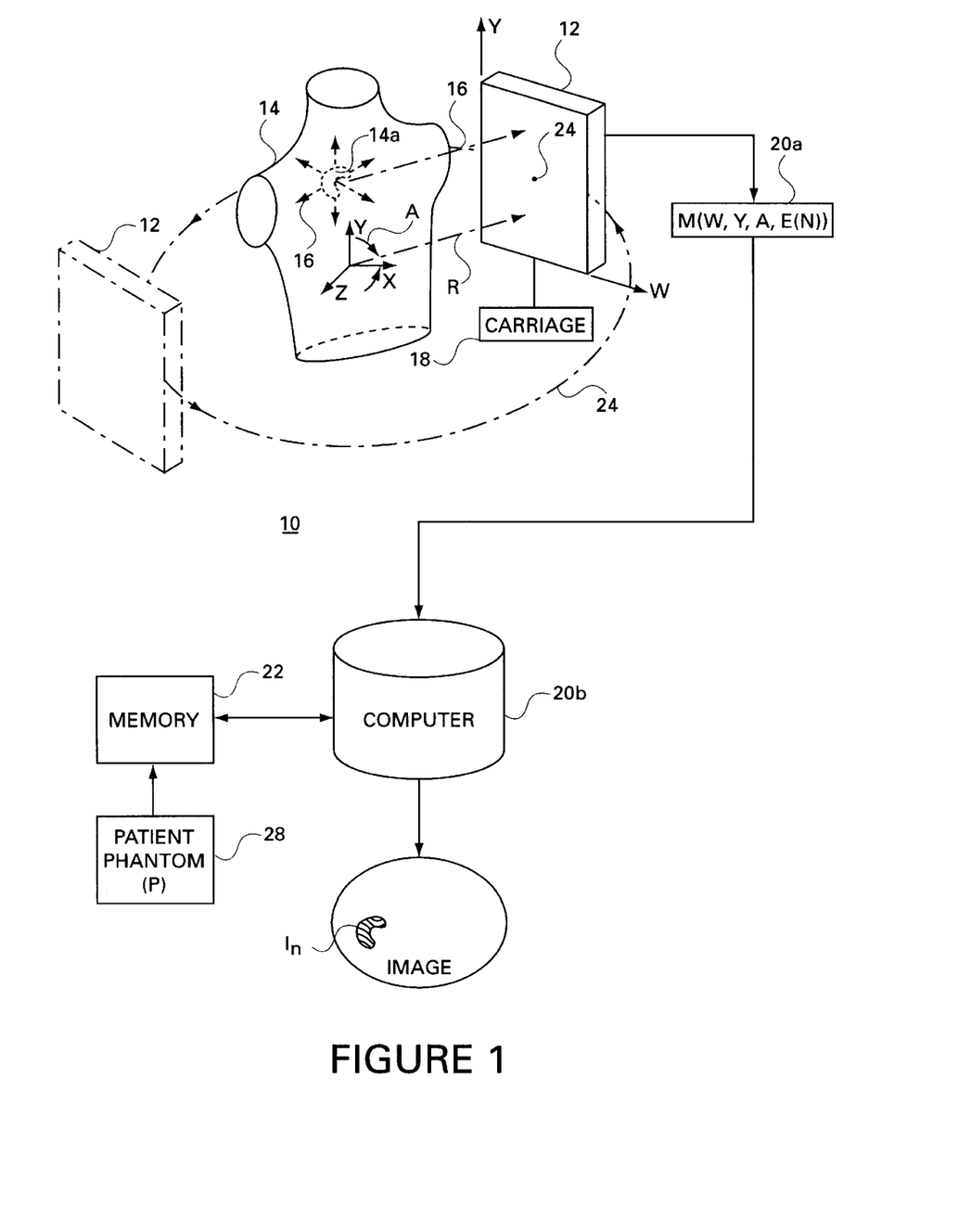
FIG. 1 is a schematic representation of an exemplary single photon computed tomography system for producing an image of a radiating source in a patient.

Illustrated schematically in FIG. 1 is a collimator-free, single photon emission computed tomography (CFSPECT) system 10 in accordance with an exemplary embodiment of the present invention. The system 10 is similar to conventional systems for effecting single photon emission computed tomography (SPECT) using a gamma camera 12, except that no mechanical or electronic collimator is used in conjunction with the camera 12, nor is the photon energy detected by the camera limited in value to a single, narrow bandwidth which detects only unscattered, or full-energy, photons.

Instead, in accordance with the present invention, the camera 12 detects all incident photons regardless of incidence angle, and over a substantially broad energy spectrum covering the entire spectral range as desired, including both unscattered photons, and single and multiple scattered photons. The additional information attendant with the uncollimated, broad spectrum photons is used to advantage to substantially reduce radiation dosage to the patient, or substantially reduce data acquisition time, or both.

Figure 2:
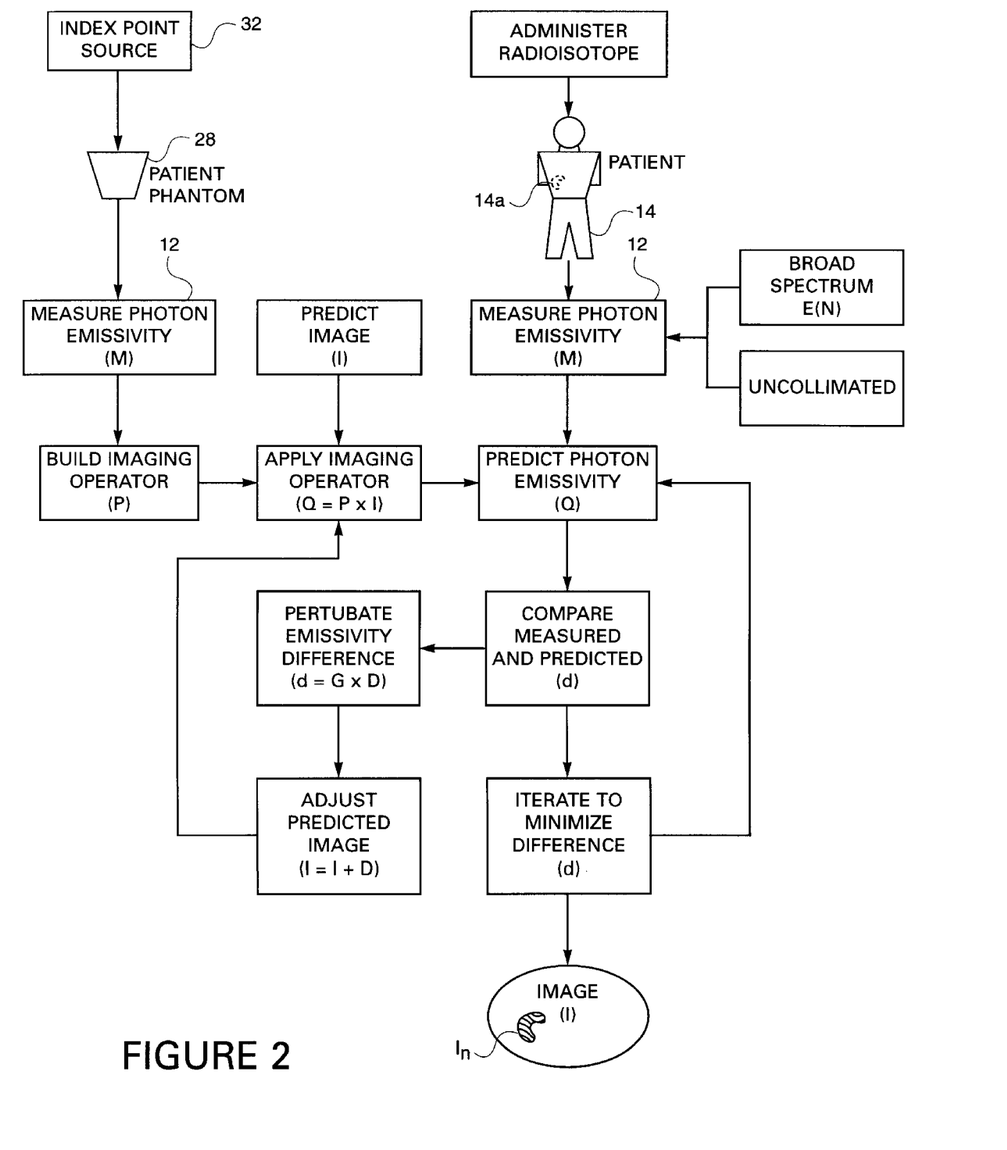
FIG. 2 is a flow chart representation of an exemplary embodiment of a method of conducting photon computed tomography on the patient illustrated in FIG. 1.

An exemplary system 10 is illustrated in FIG. 1, with a corresponding flowchart being illustrated in FIG. 2 for an exemplary method of conducting photon computed tomography for imaging a patient 14. In FIGS. 1 and 2, the patient 14 is represented schematically and has an internal organ or body 14a which is to be imaged. The method starts by administering to the patient 14 a suitable pharmaceutical labelled with a gamma emitting radioisotope, in any conventional form such as by injection, inhalation, or oral intake. The specific radioisotope is conventionally selected for targeting a desired region of the patient 14, such as in an organ or body part 14a therein. An exemplary radioisotope is $^{99m}$Tc. The radioisotope collected in the body 14a emits gamma-ray photons, or positrons which undergo annihilation with electrons in the patient 14 and produce two gamma rays emitted 180° back-to-back, which can be measured as single photons. Single photon emission computed tomography (SPECT) conventionally measures the single photons in a plurality of two dimensional arrays in a plurality of measurement views surrounding the patient, from which corresponding images of the radiation source or body are mathematically reconstructed in a computer.

In FIG. 1, the radiating or radio-emitting source is the exemplary organ or body 14a inside the patient 14 which emits single photons 16 in isotropic directions. The camera 12 is suitably positioned at a radius R from the patient 14 relative to any suitable coordinate system such as the X-Y-Z orthogonal system fixed within the center region of the patient 14.

The gamma camera 12 may take any conventional form such as the two-dimensional flat or planar camera illustrated, or it may also be curved if desired. The camera 12 may be suitably mounted in a conventional carriage 18 for revolving the camera 12 around the patient 14 in a 360° path, with the camera 12 remaining parallel to and perpendicularly facing the patient 14. One or more of the cameras 12 may be spaced apart around the patient 14 for increasing the data collection rate to thereby decrease data acquisition time. Or, the gamma camera may be stationary and configured as a fully annular camera for detecting the photons 16 simultaneously completely around the patient 14.

Figure 3:
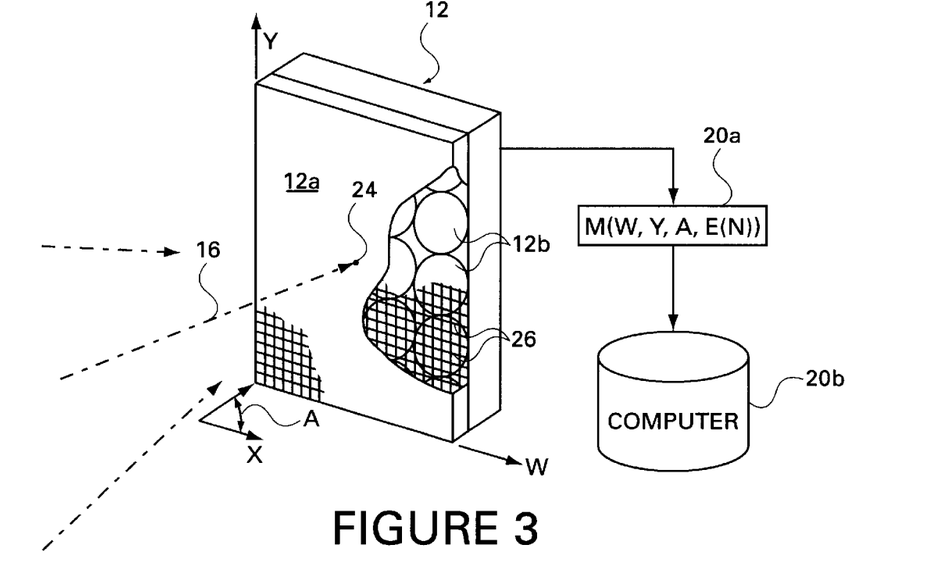
FIG. 3 is an enlarged, partly sectional view of the gamma camera illustrated in FIG. 1 in accordance with an exemplary embodiment.

FIG. 3 illustrates an exemplary embodiment of the gamma camera 12 in a conventional form, such as an Anger-type camera including a scintillator 12a configured as a flat plate which perpendicularly faces the patient 14. The scintillator 12a is conventional, and is effective for generating light upon absorbing the individual photons 16. A plurality of photodetectors 12b are arranged in a suitable two-dimensional array on the backside of the scintillator 12a and may take any conventional form including photomultipliers, or avalanche or other photodiodes. Alternatively, the camera may be made of segmented high purity diodes including germanium (HPGe), Si, CdTe, CdZnTe, HgI, or GaAs. The individual photodetectors 12b are suitably electrically joined to a conventional data acquisition electronics system 20a, and in turn to a conventional digitally programmable computer 20b as shown in FIGS. 1 and 3. The data system 20a and computer 20b collectively process the data, which is stored in a suitable computer memory 22, in the exemplary form of a hard disk memory.

The camera 12 is conventionally operated for detecting or measuring the incident gamma photons 16. For example, each incident photon 16 strikes the scintillator 12a and produces light which is simultaneously detected by one or more of the photodetectors 12b. In a conventional SPECT system, a mechanical or electronic collimator would be used in conjunction with the camera 12 for receiving photons 16 only within a narrow incidence angle substantially parallel to each other, and in most cases perpendicular to the face of the camera 12 so that the incoming direction thereof is known. Sequential photon strikes on the camera 12 are detected over a suitable sampling duration. Also in a conventional SPECT system, the data system 20a includes a suitable selection window filter specifically tuned for a given radioisotope to identify the full energy gamma photon events for which counts are made, and below and above which the photon events are discarded.

Figure 4:
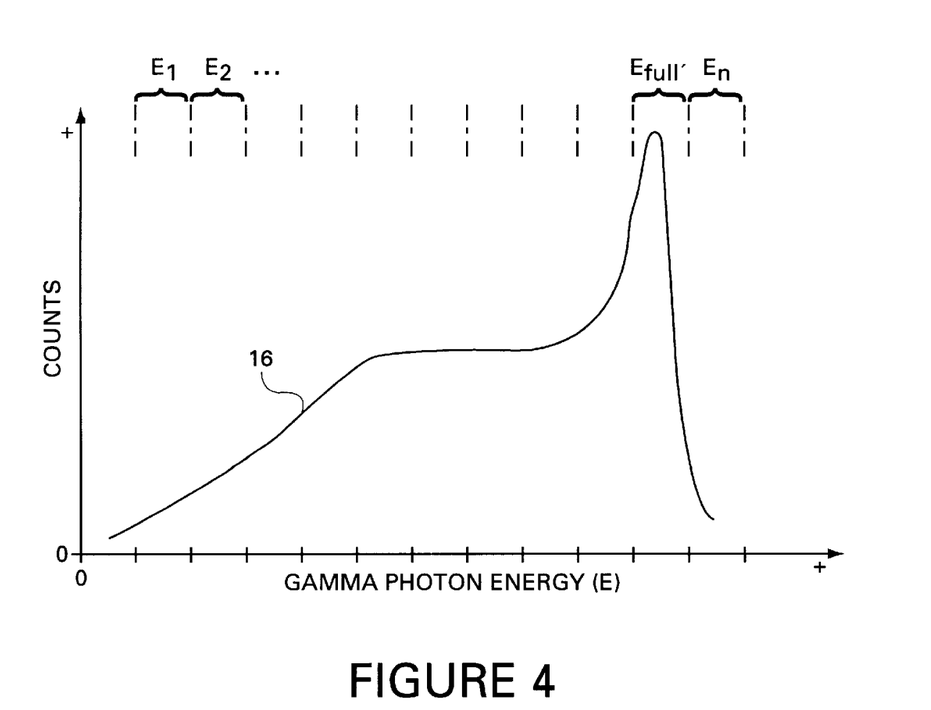
FIG. 4 is a graph plotting an exemplary energy spectrum of gamma ray photon events collected in the gamma camera as represented by counts thereof.

FIG. 4 is a graph of an energy spectrum covering a broad range of gamma ray photon energy levels for an exemplary radioisotope. An unscattered photon 16 will typically strike the camera 12 with undegraded full or peak energy $E_{full}$, whereas photons undergoing single or multiple scattering inside the patient 14 will reach the camera 12 at degraded lower energy levels. In a conventional SPECT system, the filter is provided for counting only the unscattered photon events associated with the exemplary full energy $E_{full}$.

However, and in accordance with the present invention, the gamma camera 12 illustrated in FIG. 3 is characterized by the absence of a mechanical collimator on the face of the scintillator 12a, and by the absence of any electronic collimation. And, the data acquisition system 20a is configured for counting the photon events over a desired broad energy spectrum including both unscattered events having full photon energy $E_{full}$ and single or multiple Compton scattering events in the patient 14 having lower energy levels.

Although the additional information or data provided by recording uncollimated events and also the multi-energy photon events, which include scattered and unscattered photons regardless of the photon incidence angle relative to the camera 12, increases substantially the memory space and computational effort required by the computer 20b, the additional data also allows a substantial reduction in radiation dose to the patient 14, or substantially decreases the data acquisition time, or both, while still providing resulting images at least as good as those from conventional SPECT systems.

Referring to FIGS. 1 and 2, the method includes measuring emissivity of the photons 16 externally of the patient 14 using the camera 12 at a plurality of measurement positions 24 surrounding the patient 14 for obtaining corresponding energy spectrums at each of the measurement positions. The measurement positions 24 are illustrated schematically by the individual positions of the camera 12 as it is repositioned sequentially, by rotation for example, around the patient 14 following a circular or elliptical path also designated 24. In the reference coordinate system illustrated in FIG. 1, the camera 12 faces the patient 14 and is disposed at a predetermined radius R therefrom. The angular position of the camera 12 around the patient 14 may be identified by the angular position A relative to the X-axis, for example, with there being any suitable number of angular positions of the camera 12 around the patient 14, such as one hundred twenty-eight positions at 2.8° intervals.

In the preferred embodiment illustrated in FIG. 3, the camera 12 can record photon events over a specified two-dimensional area covering the face of the scintillator 12a, and as recorded by the plurality of photodetectors 12b there below. Accordingly, the measurement positions surrounding the patient 14 preferably also each include a plurality of picture elements (pixels) 26 arranged in a predetermined and fixed two-dimensional spatial array. The number of pixels 26 is suitably larger than the number of photodetectors 12b for obtaining suitable spatial resolution. Since the camera 12 illustrated in FIG. 3 is spatially defined in space by its vertical orientation relative to the patient, and at the radius R and angular position A, the individual pixels 26 are correspondingly identified in three dimensional space. Each gamma event produces signals in many individual photodetectors 12b, from which the center of gravity is calculated and digitized in the data system 20a. The measured event is then assigned to the nearest pixel 26 location. The spatial location of the individual pixels 26 may be identified by their spatial position along the Y-axis, and along a local orthogonal axis W, with the W-Y plane being parallel to the face of the camera 12. For example, there may be one hundred pixels 26 along the W-axis and one hundred pixels 26 along the Y-axis for a total of ten thousand pixels 26 for each angular measurement position 24 of the camera 12.

In accordance with the present invention, the computer 20b is suitably configured for recording or storing in the computer memory 22 the desired broad energy spectrum of the detected photons striking the camera 12 over a plurality of incremental energy levels E(N). For example, FIG. 4 illustrates in graph form an exemplary energy spectrum including a plurality of incremental energy levels or windows $E_1$, $E_2$, ... $E_{full}$, and $E_n$. The total number n of energy windows is greater than 1, and for example may be about 20 covering the entire range of expected energy levels for a given radioisotope. The measured emissivity of the photons 16 may be obtained by conventionally counting the individual photon events over a specified sampling time for each of the energy levels E(N). The cumulative event count at each energy level or window indicates intensity of the photon events, and the collective energy levels E(N) define the entire energy spectrum.

In a conventional SPECT system, photon emissivity is determined by the counts for the single full energy $E_{full}$ level, with all other energy levels being discarded in the process. In the present invention, the additional energy levels are utilized to provide additional information associated with the primary single and multiple scattering events of the photons for reconstructing the image of the source, with unscattered photon events also being used therein.

It is to be noted that for each angular position of the camera 12 illustrated in FIG. 3, and for each sampling time thereat, an energy spectrum is obtained and stored in the computer memory 22 for each of the pixels 26. Since each energy spectrum has multiple windows, for example twenty, the collected array of data is substantially large. For the exemplary ten thousand pixels 26 illustrated in FIG. 3, each having a twenty-level energy spectrum, two hundred thousand data points are required. And, for the exemplary one hundred angular positions of the camera 12 around the patient 14, twenty million total data points are collected and stored for an entire scan of the patient 14. The measured photon emissivity is designated M in FIGS. 1–3, and is a correspondingly large matrix or array with one energy spectrum E(N) for each pixel 26 of the camera 12 at each of the angular positions A surrounding the patient 14, which is identified in three dimensional space by the coordinates W and Y, angular position A, and radius R. The array M is therefore a multiple-view set of data forming a complete tomographic set.

Without collimation of the photons 16 on the camera 12, the resulting camera image will be a nebulous cloud without direct significance. However, by effectively utilizing the probabilistic information in the entire energy spectrums E(N), a tomographic image of the radiating source 14a may nevertheless be obtained in accordance with the present invention.

Referring again to FIG. 2, the method further includes predicting in the computer 20b photon emissivity Q at the plurality of measurement positions using an initial prediction or approximation of an image designated I of the radiating source 14a, where I is a tomographic image. The predicted photon emissivity Q is provided for all corresponding measurement points, and for all corresponding levels of the energy spectrum E(N). The predicted photon emissivity Q is an array or matrix identical in form with the measured emissivity, i.e. Q(W,Y,A,E(N)).

By comparing the predicted Q and measured M photon emissivities, corresponding differences designated d therebetween may be obtained. The emissivity differences d is also an array or matrix having the same dimensions as the predicted and measured photon emissivities Q and M.

By repeating or iterating the predicting and comparing steps described above and by updating the image prediction sequentially until the differences d are below a predetermined threshold value indicative of little or no difference, the final approximation or prediction of the image $I_n$ of the source 14a may be obtained. These process steps are automatically conducted and calculated in the computer 20b specifically configured therefor.

The measured emissivity M from the gamma camera 12 represents a projection of the radiation source 14a external of the patient 14, which may be collected at incremental positions completely around the patient 14. By mathematically modeling the patient 14 and the radiation source 14a therein, the computer 20b may also be used for mathematically predicting the photon emissivity Q projected on the camera 12 at all of the measurement positions and pixels 26. By iterating the calculated prediction Q until it matches the observed or measured photon emissivity M, an accurate mathematical model of the patient 14 and the source 14a therein will be obtained from which a corresponding image of the source 14a itself may be produced.

This may be accomplished mathematically in suitable software in the computer 20b by applying a reference imaging operator designated P in FIG. 2 to an initial iteration of the image prediction, designated $I_o$, to obtain an initial prediction of the photon emissivity $Q_o$ at the plurality of pixels 26 for the plurality of measurement positions. This portion of the predicting step is represented by the matrix multiplication of the imaging operator array P and the predicted image array I, which product equals the resulting predicted photon emissivity array Q.

The imaging operator P comprises constant values which probabilistically define photon paths in the patient 14, or in the specific portion thereof being scanned. Upon congruence of the predicted and measured emissivities Q and M, the corresponding predicted image I is necessarily representative of the actual radiating source 14a in the patient 14 which produces the measured emissivity M, and has absolute, quantitative values.

Figure 5:
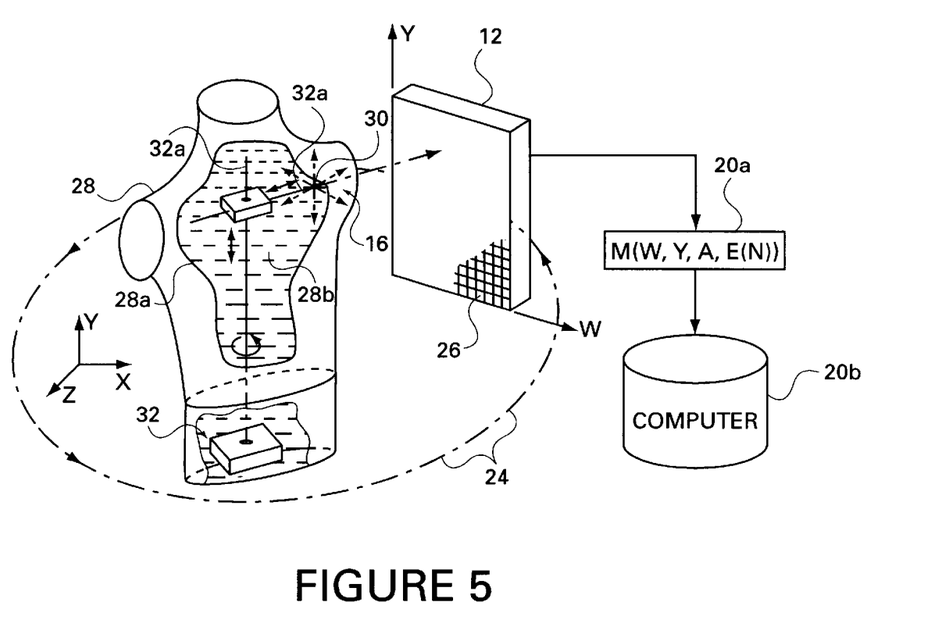
FIG. 5 is a schematic representation of a reference patient phantom corresponding to the patient illustrated in FIG. 1 for similarly measuring photon emissivity therefrom due to a radioactive point source indexed therethrough for obtaining an imaging operator used in the apparatus and method of FIGS. 1 and 2.

The imaging operator array P is obtained in advance for a specific radioisotope and for a specific configuration of the patient or portion of the patient being scanned. For example, FIG. 1 illustrates the torso as representative of the patient 14 which undergoes scanning. FIG. 5 schematically illustrates an exemplary reference model or phantom 28 which is configured or shaped to be representative of the patient 14 or corresponding portion thereof which will undergo scanning in FIG. 1.

In the exemplary configuration illustrated in FIG. 5, the phantom 28 is configured to match the outer shape of the patient torso illustrated in FIG. 1. The phantom 28 is therefore anthropomorphic to match the patient 14, and is preferably a hollow vessel having a suitable thin plastic skin 28a which is filled with a suitable liquid 28b such as water, or tissue-equivalent material. The phantom 28 is used in accordance with the present invention to provide a calibration data set as represented by the imaging operator P which allows reconstruction of the measured emissivity M into a three-dimensional image I of the radiation source 14a.

Figure 6:
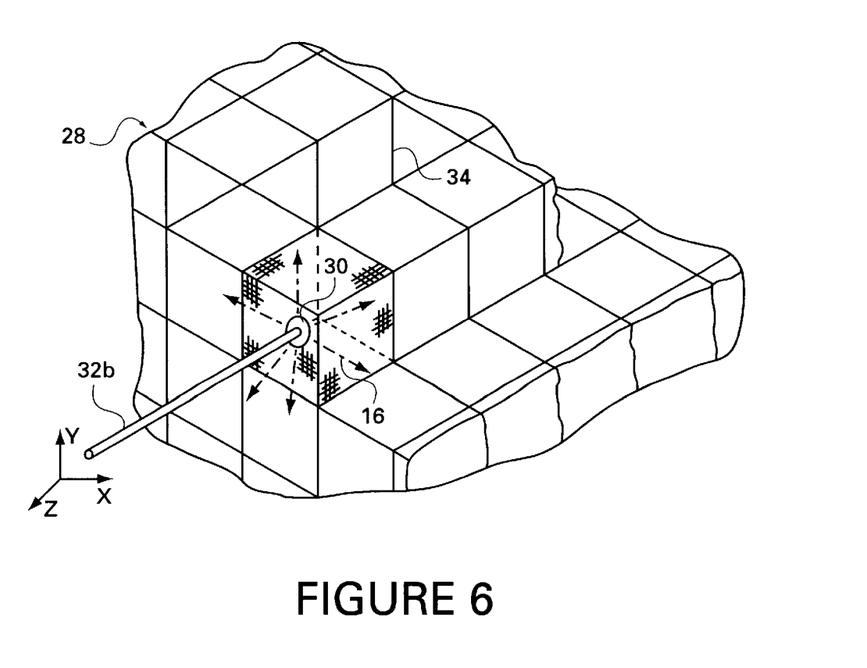
FIG. 6 is an enlarged isometric view of a portion of the phantom illustrated in FIG. 5 with the point source disposed in one of several schematically illustrated volume element voxels.

More specifically, FIG. 5 illustrates that a reference point source 30 of the same radioisotope used in the scanning system 10 of FIG. 1 is provided inside the phantom 28 for producing gamma ray photons 16 therein. A suitable indexing apparatus 32 is provided at a suitable location, such as below the main portion of the phantom 28, for suitably positioning or indexing the reference source 30 incrementally inside the phantom 28 at a plurality of calibrating positions therein of sufficient resolution to define a respective plurality of contiguous volume elements or voxels 34, illustrated in enlarged view in FIG. 6. The voxels 34 collectively define the entire volume of the phantom 28 which corresponds with the desired volume of the patient 14 to be scanned, and define the image (I). And, the voxels 34 collectively define the 3-D geometric boundary of the image I, and have a suitable quantity to provide suitable resolution of the voxel image I.

The indexing apparatus 32 may take any suitable form including for example two intersecting screw rods 32a,b, with the reference source 30 being fixedly joined to the end of the second rod 32b. The reference source 30 may then be positioned voxel-by-voxel 34 by adjusting the length of the second rod 32b and angular position relative to the first rod 32a, as well as adjusting the vertical height of the second rod 32b on the first rod 32a. In this way, the reference source 30 may be centered in each voxel 34 in turn. Since each voxel 34 defines an element of the phantom 28, they are preferably as small as practical, with the reference point source 30 being suitably smaller for fitting inside an individual voxel 34. For example, there may be a thousand or more voxels 34 in each phantom 28 as desired for providing a suitable amount of resolution for providing imaging of the actual patient 14.

By assigning an intensity value to individual voxels 34, any image I within the resolution of the voxels 34 may be generated. The predicted image I is an array which corresponds with the total number of voxels 34, with each voxel 34 being identified in three dimensional space by its X, Y, Z coordinates. Accordingly, it is preferred that the X-Y-Z coordinate system associated with the phantom 28 in FIG. 5 is the same as the X-Y-Z coordinate system in the scanning system 10 illustrated in FIG. 1.

The phantom 28 is preferably positioned in the same scanning system 10 of FIG. 1 for rotating the gamma camera 12 therearound as described above, and illustrated in FIG. 5. The scanning system 10 should be operated identically for the phantom 28 as it is for the patient 14 for producing the corresponding, mutually sized array of measured photon emissivity M for each of the pixels 26 at the coordinates W, Y, A, and at the same radius R, with an identically sized energy spectrum E(N) for each pixel 26, at each measurement position 24.

Accordingly, the scanning system 10 and camera 12 are utilized in FIG. 5 for measuring emissivity of the photons 16 emitted from the phantom 28 externally thereof due to the point source 30 incremented from voxel 34 to voxel 34. At each voxel position of the point source 30, the photon emissivity as represented by the broad spectrum E(N) is measured at each of the measurement positions and pixels. In this way, a complete data set of broad spectrum emissivity E(N) is obtained for each pixel of the camera 12 at each measurement position around the phantom 28. The imaging operator P is therefore an array of the measured voxel photon emissivity E(N) due to each of the irradiated voxels independently, and thus provides influence coefficients representing the independent photon radiating effect from each voxel on each pixel at the different measurement positions per scan revolution. In this way, the tomography system 10 is specifically calibrated for non-collimated, broad energy spectrum tomography of the patient 14.

In the trivial case of the radiating source 14a being identical to the point source 30 at any individual location within the patient 14, the image I thereof will be readily obtained through few iterations since the imaging operator P inherently includes a measured emissivity M from the phantom 28 which will be substantially identical to a corresponding measured emissivity M from the patient 14.

In the nontrivial case wherein the radiating source 14a extends in a complex configuration over many analogous voxels with varying intensity, the iteration process is prolonged as the initial prediction of the image $I_o$ is sequentially updated and applied to the imaging operator P to successively predict the photon emissivity Q for reducing the difference d thereof with the measured emissivity M.

In all cases, an initial prediction of the voxel image $I_o$, may be selected as desired, with the initial value of the array $I_o$ being a constant value for each element thereof in a simple example. In the next step, the imaging operator P as shown in FIG. 2 is applied or multiplied with the initial image prediction $I_o$ in the computer 20b to obtain an initial prediction of the photon emissivity $Q_o$, and is then suitably updated to reach a final predicted image $I_n$ representative of the radiating source 14a in the patient 14, where n is any suitably large number which ends the iteration process.

The imaging operator P may be defined as a quantity whose physical interpretation is the probability distribution of photons that travel from a source to an arbitrary point in a medium, and from this point to the gamma camera, integrated over all space. Phenomenologically this distribution looks like a cloud. It has fuzzy corners, and its density varies with space, usually at its largest in the vicinity of the source. As indicated above, the imaging operator P may be measured directly by moving a point source inside the phantom 28. Since the camera 12 is without a collimator, the direct, perpendicular unique path thereto typically found in SPECT systems no longer exists. But, instead, a spatial probability distribution of paths exist. Although the individual path cannot be determined, the ensemble average can, and even with high precision, and is represented by the imaging operator P.

Once the entire set of measured data M is obtained from scanning the patient 14, reconstruction of the radiating source 14a may then be accomplished in the computer 20b using the imaging operator P. The iterative process introduced above is sometimes referred to as the Green's function method which is conventionally known. As applied to the present invention, this process starts with an initial approximation or guess of the distribution of radioisotope in the subject's body. The imaging operator P is then applied to the initial image prediction $I_o$ to calculate the camera or projection images represented by the image photon emissivity Q analogous to the expected measured photon emissivity M. Application of the imaging operator P constitutes a solution to a forward problem. The imaging operator is in effect a product of two partial operators, or Green's functions including one that characterizes the geometry and temporal properties of the source and camera as represented by the imaging system 10, and a second one that characterizes the physical properties of the medium, such as its composition and geometry, and therefore changes from one patient to another.

The invention uses an image reconstruction process generally known mathematically as an inverse source problem. The goal is to reconstruct the distribution of sources based on measurements performed outside of a target medium. In practice, inverse source problems can involve spontaneously emissive sources such as radioisotopes, or include fluorescent emissive sources.

The inverse problem in the case of the present invention can be cast as a system of linear equations, just as in conventional near infrared (NIR) diffusion imaging and fluorescence imaging. Thus, the image is computed by solving the equation $d=G \times D$, where d is the array or matrix of differences between the measured and predicted emissivities, i.e. camera readings M and Q, respectively; G is the Green's function, which is the same as the imaging operator P; and D is the respective array of differences between the true and predicted, or estimated, image I represented by the source strengths in the interior of the target medium. In other words, by perturbating the emissivity differences d in each of the iterating steps to obtain respective changes D in the predicted image I at each of the voxels 34, solution of the inverse problem may be rapidly obtained.

The Green's function equation $d=G \times D$ can be solved for an arbitrary media using any of a number of conventionally known numerical computational methods. The perturbation equation described above is a set of linear equations that can be solved in a variety of iterative ways. It is also generalized in accordance with the present invention to cover the multiple energy windows E(N). In this case, a different Green's function G is used for each energy window $E(1,2,3,\ldots,N)$.

In practice, measurements are made from the multiple views of the camera 12 to provide a complete tomographic data set. The corresponding set of Green's function is commonly referred to as a Jacobian matrix. Solutions to the perturbation equation can be accomplished using standard Newton-type or similar iterative algorithms based on Born or Rytov solutions. These can be based on analysis of data corresponding to single or multiple energy windows. When data from multiple energy windows are considered, a corresponding adjoint Green's function would be computed for each energy window. Two approaches commonly used are referred to as the iterative Born method, known also as the Newton-Kanatorovich method, and the distorted Born method. Whereas the former considers a more approximate solution and updates only the Green's function, both methods involve recursive iterative solution to the forward and inverse problems.

Simply stated, the Green's function method may be used in each iterating step to produce the image difference array D as shown in FIG. 2. The initial prediction of the image $I_o$ may then be updated by adding thereto the so calculated differences $D_o$ to provide the next predicted image $I_1$.

The second iteration is then conducted by applying the imaging operator P with the updated predicted image $I_1$ to obtain the next predicted photon emissivity $Q_1$. Another difference between the measured and predicted emissivity M and $Q_1$ is obtained, i.e. $d_1$. If these differences $d_1$ are not within the desired minimum threshold, the iteration is then repeated. In which case, a new perturbation of the emissivity differences $D_1$ is obtained and added to the last predicted image $I_1+D_1$ to obtain the next predicted image $I_2$ and the process is repeated.

The final image $I_n$, as n becomes a relatively large number will be obtained when the compared difference $d_n$ of the measured and predicted emissivities becomes a suitably small value approaching zero. The final image $I_n$ represents the phantom equivalent of the actual radiation source 14a.

Although a considerable number of data points are obtained and stored in the computer memory 22 for each tomographic data set; and a considerable number of data points representative of the imaging operator P for the patient phantom 28 are also stored in the computer memory 22; and although the forward and inverse problems include large array equations, conventional mainframe computers are presently available for manipulating and calculating the data as required for solving the various equations and performing the required number of iterations in order to obtain the final prediction of the image $I_n$ representative of the actual radiation source 14a which produces the tomographic data.

The final image $I_n$ is a three dimensional representation of the distribution of the radiation source 14a and may therefore be viewed as suitable two dimensional transaxial slices, or three dimensional images, as desired for medical diagnosis purposes.

As indicated above, various conventional mathematical techniques are available for perturbating the emissivity differences d to obtain suitable changes D for updating the predicted image I. And, conventional mathematical techniques are available for mathematically manipulating the data and solving the various equations leading to the final iteration and solution and reconstruction of the image $I_n$.

It is noted that the phantom 28 is homogeneous since it is used for creating the required imaging operator P which is indicative of the expected measured emissivity M attributable to each voxel 34 of the phantom 28. The actual patient, in contrast, includes various organs and organ density which differently attenuates the photons 16 traveling therethrough. Photon attenuation is a common problem in conventional SPECT systems, and conventional compensation therefor exists and may be similarly applied in the present invention for improving the quality of the final image $I_n$.

As indicated above, the additional information provided by the broad spectrum of the uncollimated measured photon emissivity M provides additional information for improving the imaging process. Because of the absence of the collimator, for the same amount of radioactivity in the subject, the count rate in the camera 12 will be three to four orders of magnitude higher than that of the conventional SPECT system. As indicated above, the improved method requires significantly less radioactivity for the same imaging information, and therefore it reduces the absorbed dose to the patient.

Because of the high detection sensitivity of the uncollimated camera 12, the system 10 should have an excellent count-rate capability compared to conventional gamma cameras. Count-rate capability means good performance at high count rates. For example, the energy resolution of the system 10 may be better than 10% full-width-at-half-maximum (FWHM) for 140 keV up, at count rates as high as 200,000 per second. Depending on the administered activity, activity distribution in the patient, and camera sensitivity, the count rate during a typical measurement can be one to two orders of magnitude higher than that in a typical conventional SPECT clinical study.

Since the gain in the camera sensitivity is three to four orders of magnitude, this means that the amount of radioactivity in the radio-pharmaceutical administered to the patient will be about two orders of magnitude smaller than that used in conventional SPECT. This means that the data collection times are generally shorter, and the radiation absorbed doses are generally smaller in the present invention compared to conventional SPECT systems.

Accordingly, the method in accordance with the present invention requires significantly less radioactivity for the same imaging information, and therefore, it reduces the absorbed dose to the patient. And, the higher count-rate capability allows a significant reduction in data collection time. It is estimated that the spatial resolution of the system 10 should be better than about 4 mm FWHM for the same count rate of 200,000 counts per second.

As indicted above, various conventional mathematical procedures may be used for solving the forward and inverse problems in reconstructing the image from the new, non-collimated broad energy spectrum photon counts measured in a complete scan. Another example is to use methods which fall into the category of statistical image reconstruction. This includes methods such as Maximum Likelihood and Maximum Entropy, and is generally called Expectation Maximization. The method can use any of a number of standard approaches commonly used to solve nonlinear inverse problems. In particular, these solutions can use as prior knowledge, images obtained with other imaging modalities, such as computerized axial tomography (CAT) scanners or magnetic resonance imaging (MRI). Use of this information would serve to define a reference state that more closely approximates the unknown medium under study. It is also recognized that neural net solutions may also be used within this category of reconstruction methods, using training sets that comprise linear combinations of the value of the product side (G×D) of the Green's perturbation equation described above.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims:

We claim:

1. A method of photon computed tomography comprising:
   administering a radioisotope to a patient (14) for producing gamma ray photons (16) from a source (14a) inside said patient;
   measuring emissivity of said photons (16) externally of said patient (14) at a plurality of measurement positions (24) surrounding said patient (14) for obtaining corresponding energy spectrums (E);
   predicting photon emissivity (Q) at said plurality of measurement positions (24) using an initial prediction of an image (I) of said source (14a);
   comparing said predicted and measured photon emissivities (Q,M) to obtain differences (d) therebetween; and
   iterating said predicting and comparing steps by updating said image prediction (I) until said differences (d) are below a threshold for obtaining a final prediction of said image ($I_n$).

2. A method according to claim 1 further comprising measuring said photon emissivity uncollimated.

3. A method according to claim 2 wherein:
   said energy spectrum (E) includes a plurality of incremental energy levels (1,2,3, . . . ,N); and
   said measured emissivity (M) includes a corresponding intensity for each of said energy levels at each of said measurement positions.

4. A method according to claim 3 wherein said measurement positions each include a plurality of pixels (26) arranged in a two-dimensional spatial array, with each pixel (26) having a corresponding one of said energy spectrums (E).

5. A method according to claim 4 wherein said predicting step comprises applying a reference imaging operator (P) to said image prediction (I) to obtain said predicted photon emissivity (Q) at said plurality of pixels (26) for said plurality of measurement positions.

6. A method according to claim 5 wherein said reference imaging operator (P) is obtained by:
   providing a reference source (30) of said radioisotope inside a phantom (28) representative of said patient (14) for producing gamma ray photons (16) therein;
   indexing said reference source (30) incrementally inside said phantom (28) at a plurality of positions therein to define a respective plurality of volume element voxels (34) collectively defining said phantom (28); and
   measuring emissivity of said photons (16) emitted from said phantom (28) externally thereof at each of said measurement positions for obtaining corresponding energy spectrums (E) threat for each of said incrementally scanned voxels (34), with said imaging operator (P) being said measured voxel photon emissivity (E) due to each of said irradiated voxels (34) independently.

7. A method according to claim 6 wherein said phantom (28) comprises an anthropomorphic hollow vessel filled with liquid (28b).

8. A method according to claim 6 wherein said voxels (34) define said predicted image (I).

9. A method according to claim 8 further comprising:

perturbating said emissivity differences (d) in each of said iterating steps to obtain respective changes (D) in said predicted image (I) at each of said voxels (34); and adjusting said predicted image (I) at each of said iterating steps using said image changes (D).

10. A method according to claim 9 wherein said perturbating step comprises Green's function.

11. A photon computed tomography system (10) for imaging a source (14a) in a patient (14) producing gamma ray photons (16) comprising:

means (12) for measuring emissivity of said photons (16) externally of said patient (14) at a plurality of measurement positions (24) surrounding said patient (14) for obtaining corresponding energy spectrums (E);

means (20b) for predicting photon emissivity (Q) at said plurality of measurement positions (24) using an initial prediction of an image (I) of said source (14a);

means (20b) for comparing said predicted and measured photon emissivities (Q,M) to obtain differences (d) therebetween; and means (20b) for iterating said predicting and comparing steps by updating said image prediction (I) until said differences (d) are below a threshold for obtaining a final prediction of said image ($I_n$).

12. A system according to claim 11 wherein said measuring means comprise an uncollimated gamma camera (12).

13. A system according to claim 12 wherein:

said energy spectrum (E) includes a plurality of incremental energy levels (1,2,3, . . . ,N); and said measured emissivity (M) includes a corresponding intensity for each of said energy levels at each of said measurement positions.

14. A system according to claim 13 wherein said camera (12) includes a plurality of pixels (26) arranged in a two-dimensional spatial array, with each pixel (26) having a corresponding one of said energy spectrums (E).

15. A system according to claim 14 wherein said means for predicting, comparing, and iterating comprise a computer (20b) configured for performing said steps.

16. A system according to claim 15 wherein said computer (20b) is configured for applying a reference imaging operator (P) to said image prediction (I) to obtain said predicted photon emissivity (Q) at said plurality of pixels (26) for said plurality of measurement positions.

17. A system according to claim 16 further comprising:

a reference source (30) of said radioisotope inside a phantom (28) representative of said patient (14) for producing gamma ray photons (16) therein;

means (32) for indexing said reference source (30) incrementally inside said phantom (28) at a plurality of positions therein to define a respective plurality of volume element voxels (34) collectively defining said phantom (28); and said camera (12) being effective for measuring emissivity of said photons (16) emitted from said phantom (28) externally thereof at each of said measurement positions for obtaining corresponding energy spectrums (E) thereat for each of said incrementally scanned voxels (34), with said imaging operator (P) being said measured voxel photon emissivity (E) due to each of said irradiated voxels (34) independently.

18. A system according to claim 17 wherein said phantom (28) comprises an anthropomorphic hollow vessel filled with liquid (28b).

19. A system according to claim 18 wherein said computer (20b) is further configured for:

perturbating said emissivity differences (d) in each of said iterating steps to obtain respective changes (D) in said predicted image (I) at each of voxels (34); and adjusting said predicted image (I) at each of said iterating steps using said image changes (D).

* * * * *